United States Patent [19]

Ceravolo

[11] Patent Number: 5,292,346
[45] Date of Patent: Mar. 8, 1994

[54] BACTERICIDAL THROAT GUN

[76] Inventor: Frank J. Ceravolo, 2877 NE. 29th St., Fort Lauderdale, Fla. 33306

[21] Appl. No.: 837,898

[22] Filed: Feb. 20, 1992

[51] Int. Cl.⁵ .............................................. A61N 5/06
[52] U.S. Cl. ....................... 607/80; 128/11; 128/13; 128/16; 604/20; 604/21; 606/2
[58] Field of Search ............... 128/395, 396, 787, 800, 128/3, 11, 13, 15, 16, 22, 23; 604/20, 21, 26; 606/2, 13, 15, 17

[56] References Cited

U.S. PATENT DOCUMENTS

| 1,735,215 | 11/1919 | Schwanzel et al. | 362/262 |
| 1,908,010 | 5/1933 | Cameron | 128/16 |
| 1,932,473 | 10/1933 | Morgan et al. | 128/16 |
| 1,939,413 | 12/1933 | Robinson | 128/395 |
| 2,255,657 | 9/1941 | Freedman | 128/23 |
| 2,326,773 | 8/1943 | Floyd | 362/293 |
| 2,383,421 | 8/1945 | Schultz | 128/395 |
| 2,439,787 | 4/1948 | Atkins | 128/395 |
| 2,745,407 | 5/1956 | Mueller et al. | 128/107 |
| 3,527,932 | 9/1970 | Thomas | 240/6.4 |
| 4,159,411 | 6/1979 | Ellersick | 219/346 |
| 4,273,112 | 6/1981 | Heine et al. | 128/11 |
| 4,344,419 | 8/1982 | Burgin | 128/3 |
| 4,535,784 | 8/1985 | Rohlicek et al. | 128/735 |

FOREIGN PATENT DOCUMENTS

| 3023130 | 1/1982 | Fed. Rep. of Germany | 128/395 |
| 0714070 | 11/1931 | France | 604/26 |
| 1614808 | 12/1990 | U.S.S.R. | 604/21 |
| 2208803 | 4/1989 | United Kingdom | 128/395 |

Primary Examiner—Jessica J. Harrison
Attorney, Agent, or Firm—Oltman and Flynn

[57] ABSTRACT

A bactericidal ultraviolet light radiating device for treatment of mucosal or dermal tissues, having an ultraviolet light source, an optical light-directing lens optically coupled to the ultraviolet light source for directing the ultraviolet light to the mucosal or dermal tissues, an electric power supply connected to the ultraviolet light source for supplying electric power for the ultraviolet light source and a medication dispensor coupled to the ultraviolet light source for applying a medication to the mucosal or dermal tissues. The device is primarily intended for oral (pharynx, gums, etc.) therapeutic radiation application as well as for all body cavities (nasal, ear, etc.) and for dermal pathology (ulcers, cellulitis, etc.).

15 Claims, 4 Drawing Sheets

BACTERICIDAL THROAT GUN

The invention relates to a bactericidal throat gun for applying ultraviolet light radiation to mucosal or dermal tissue, either alone or combined with the application of a bactericidal agent to the tissue.

BACKGROUND AND PRIOR ART

It is well known that ultra-violet light has bactericidal effect. Earlier inventions have disclosed forms of ultraviolet light generators that can be used to direct ultraviolet ("UV") light to certain infected body areas. U.S. Pat. No. 2,439,787 shows an example of such an ultraviolet ray generator. U.S. Pat. No. 1,735,215 shows a curative ray generator that operates to irradiate body parts with ultraviolet light generated by a carbon arc.

Ultraviolet radiation alone is often not adequate to treat deeper seated bacterial infections, and prolonged exposure to ultraviolet light can be detrimental to human tissues. It is therefore of great advantage to combine ultraviolet radiation therapy with complementary bactericidal therapy, e.g. in the form of topical treatment with suitable medications such as antibiotic, antiseptic, anesthetic and/or soothing liquids.

It is accordingly an object of the invention to provide a bactericidal device which provides simultaneous treatment with ultraviolet radiation and liquid medications for even more effective therapy.

SUMMARY OF THE INVENTION

In accordance with the invention there is provided a bactericidal ultraviolet light radiating device for treatment of mucosal or dermal tissues, having an ultraviolet light source, optical light-directing means optically coupled to the ultraviolet light source for directing the ultraviolet light to the dermal tissues, electric power supply means connected to the ultraviolet light source for supplying electric power for the ultraviolet light source and medication dispensing means coupled to the ultraviolet light source for applying a medication to the mucosal or dermal tissues.

The bactericidal ultraviolet radiation device according to the invention further includes a curved reflector disposed behind the ultraviolet light source in the optical light directing means, and may additionally include an optical condensing quartz lens disposed ahead of the ultraviolet light source in the light-directing means for condensing the ultraviolet light.

According to a further feature the dispensed medication may include a bactericide, an anesthetic, an antiseptic, an antibiotic and/or a soothing agent to the mucosal or dermal tissue, and the device includes trigger means for triggering the application of the medicinal agent.

According to still another feature there is provided an aerosol dispenser in the radiation device, a pressure-sensitive valve on the aerosol dispenser, a trigger in the trigger means coupled to the valve for activating the spray valve, and a forward facing nozzle connected to the valve for forwardly directing a spray of the medicinal agent upon activation of the valve.

The invention may further include a power converter in the electric power supply means, and at least one electric battery connected to the power converter, wherein the electric battery can be an electric storage battery, and activating linkage coupling the trigger means to the electric switch.

The bactericidal ultraviolet radiating device may advantageously include light concentrating means in the optical zoom light directing means, including optical fiber conducting means in the light concentrating means for concentrating light to a thin ray of ultraviolet light.

The bactericidal ultraviolet radiating device may advantageously include a forward-facing slot in the radiating device for holding a tongue depressor in the slot, and a container for containing the aerosol dispenser, and a retractable screw cover at the bottom of the container for retracting the dispenser beyond reach of the trigger.

Further objects and advantages of this invention will be apparent from the following detailed description of a presently preferred embodiment which is illustrated schematically in the accompanying drawings.

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

DESCRIPTION OF THE PREFERRED EMBODIMENTS

Figure 1:
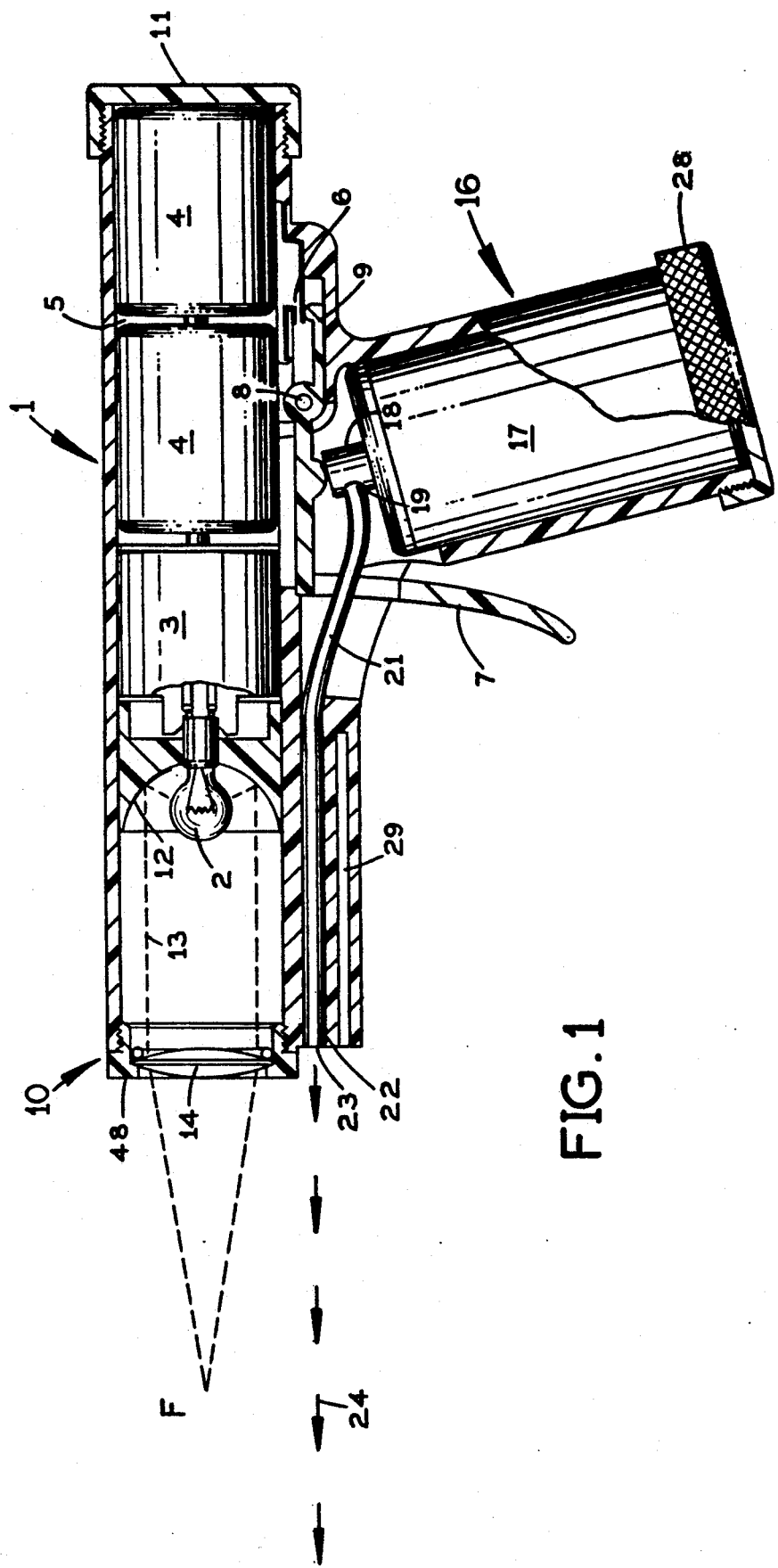
FIG. 1 is an elevational diagrammatic view of the invention with part of the wall broken away to show the interior construction.
Figure 2:
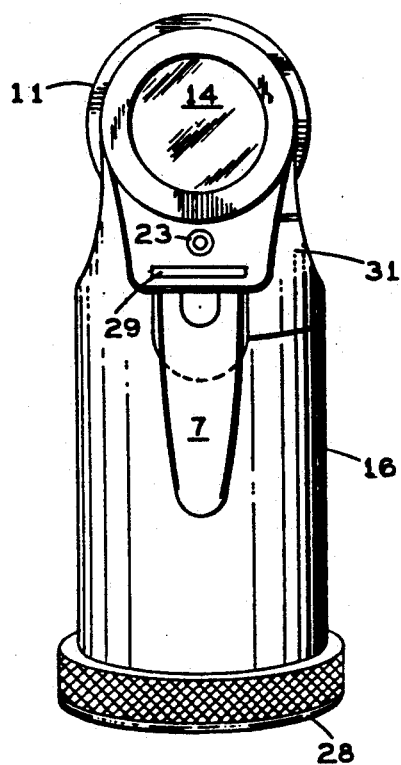
FIG. 2 is a front elevational view of the invention.
Figure 3:
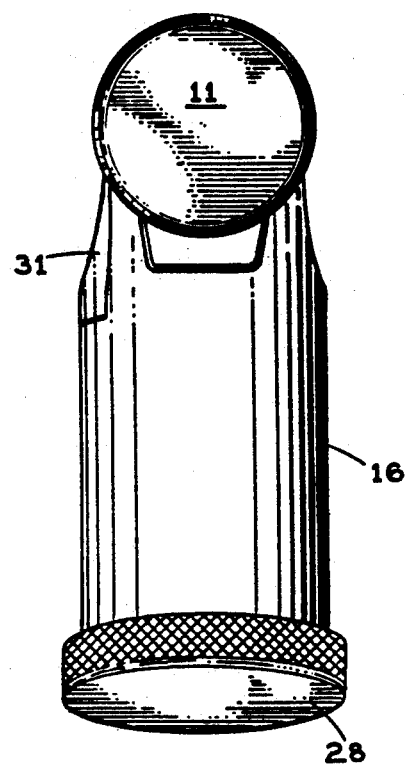
FIG. 3 is a rear elevational view of the invention.

In FIGS. 1, 2 and 3, a housing 1 has an elongate interior cavity 5 for holding at its forward end an ultraviolet light source 2 of a compact type, manufactured for example by General Electric under the designation G4S11, although several other suitable types are available from G.E. and other manufacturers. The ultraviolet light source 2 is powered by an electric power converter 3 that contains various electrical components as required to operate the ultraviolet light source 2, as described in more detail below. The power converter 3 may receive its primary electric power from, for example, electric storage batteries 4, e.g. so-called Ni-Cad batteries, or it can be powered by commercial ac power via a power cord, not shown. The storage batteries 4 are connected to the power converter 3 via an electric on-off switch 6 that is activated by a trigger 7 pivotally mounted on a pivot point 8, and having a rearwardly extending linkage or projection 9 that activates the switch 6 when the trigger 7 is operated. A screw-cover 11 at the rear of the housing 1 can be removed to gain access to the storage batteries 4 so that they can be removed for recharging or replacement with freshly charged batteries.

The ultraviolet light source 2 is advantageously mounted with a curved reflector 12 behind it. The curved reflector can be shaped as a paraboloid with the ultraviolet light emitting element 2 located in or near the focal point of the reflector, so that the reflected UV-rays 13 extend forward substantially as a bundle of parallel rays 13. The reflector can slide for the purpose of restricting or enlarging the area of radiation.

Various optical elements can be placed at the nose 10 of the device, e.g. in the form of a condensing lens 14 of a UV-translucent material, such as quartz or the like, which concentrates the UV-rays at a focal point F where the intensity of the UV-radiation is at its maximum. The condensing lens 14 can be replaced by other types of condensing elements as described in more detail below. The condensing lens can be a zoom lens.

The housing 1 has a downward facing chamber 16 for holding a container 17 containing a liquid or powdery medication. The container 17 may advantageously be an aerosol can containing a liquid antibiotic, antiseptic, anesthetic and/or soothing (or combination) medication together with a suitable propellant as is well known from aerosol dispensers.

The container 17 has a conventional top valve 18 which, when depressed, releases the contents of the container 17. The valve 18 has a recess 19 that permits an end of a flexible hose or tube 21 to be inserted in the recess of the valve 18. The tube 21 is conducted through a channel 22 in the housing with the other end 23 of the tube projecting forward so that a spray 24 of the medication can be propelled forward when the valve 18 is activated by the trigger 7.

Figure 7:
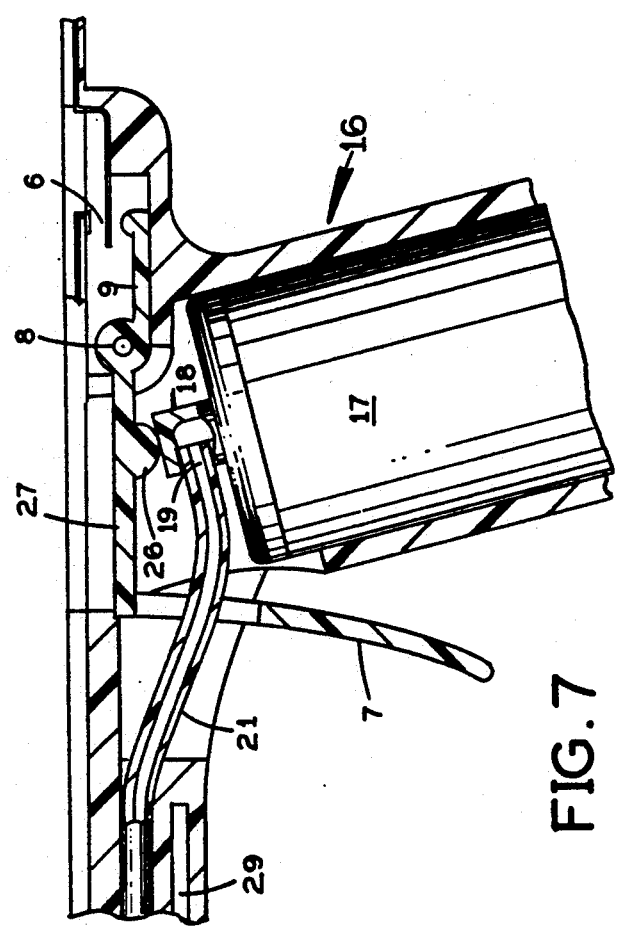
FIG. 7 is a fragmentary detail drawing showing details of the valve and trigger arrangement.

The valve 18 is activated by the trigger 7 as shown in more detail in the fragmentary detail FIG. 7 wherein the trigger 7 has a pivot arm 27 pivotally attached at one end to the housing 1, via pivot point 8. A downward facing cam 26 on the arm 27 engages the top of the valve 18 to release the contents of the can 17 via tube 21 when the trigger 7 is operated.

A bottom screw cap 28 is threadedly attached to the bottom of the chamber 16 to enable replacement of the aerosol can 17. A side door 31 best seen in FIGS. 2 and 3, provides access to the valve 18 and the tube 21 so that the tube 21 can be inserted into the recess 19 of the valve 18 after a spent aerosol can 17 has been replaced.

Figure 6:
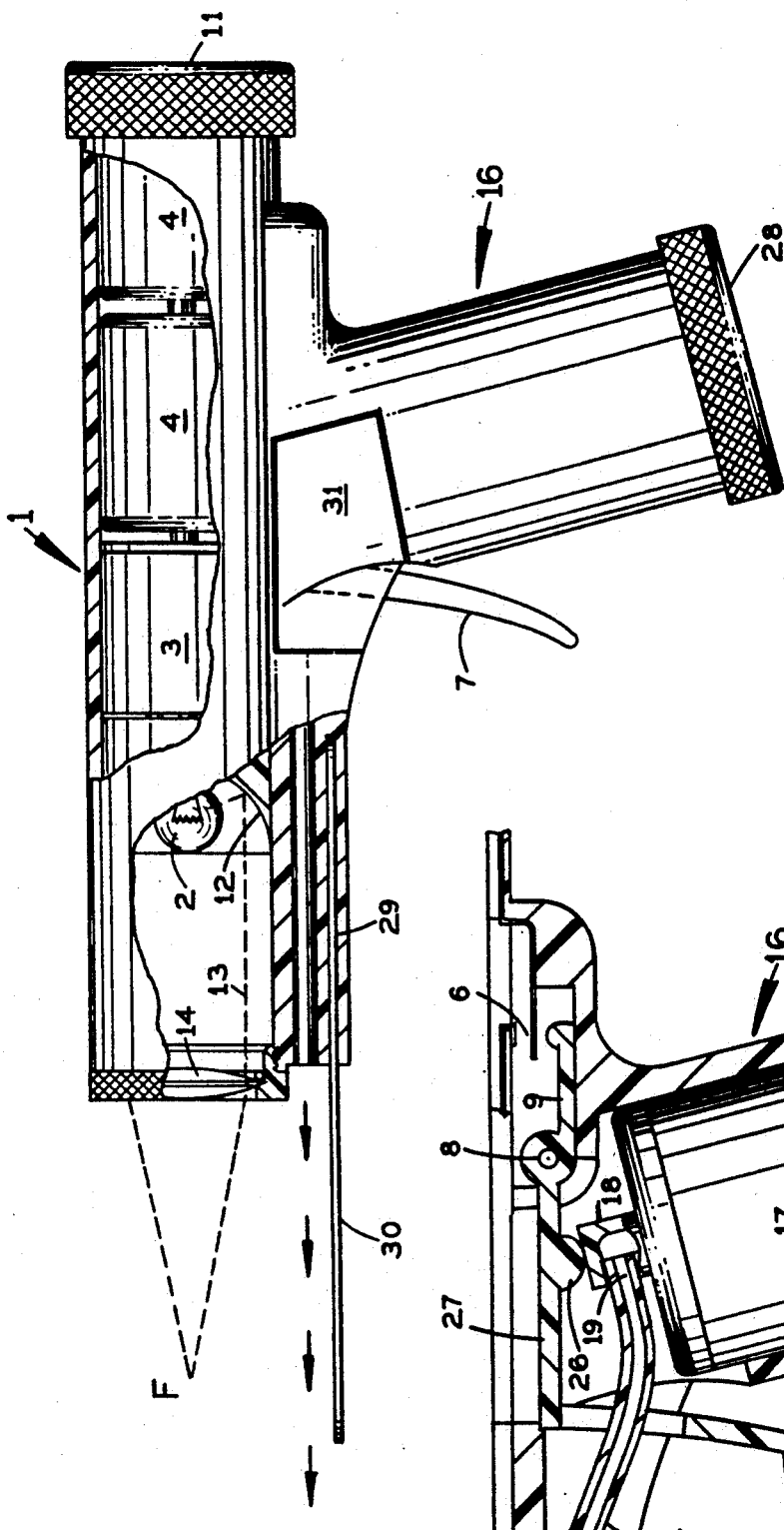
FIG. 6 is an elevational view of the invention showing a slot for insertion of a tongue depressor.

A slot 29 provides means for inserting a flat tongue depressor 30 best seen in FIG. 6.

Figure 4:
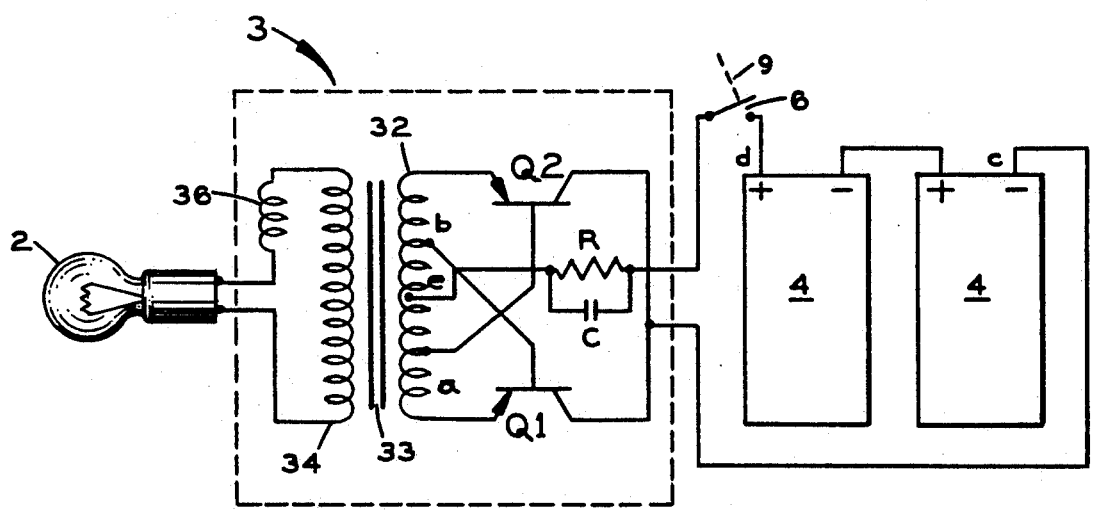
FIG. 4 is a block diagram of the invention showing the electrical circuit.

FIG. 4 is a circuit diagram showing details of the power converter 3, which includes a dc-dc-converter including two transistors Q1, Q2 having their emitters connected to opposite ends of a primary winding 32 of a transformer 33. The transistor bases are cross connected to taps a, b of the primary winding 32, and the commonly connected transistor collectors are connected to the negative terminal c of batteries 4, while the positive terminal d is connected via switch 6 to centertape of primary winding 32 via a parallel resistor-capacitor assembly C,R. As the switch 6 is closed by linkage 9 of the trigger 7, transistors Q1, Q2 start oscillations in the primary winding 32, which are voltage-transformed through transformer 33 to a higher operating voltage in the secondary winding 34, which feeds the UV-light source 2 through a ballast inductor 36. The dc-dc converter 3 can be configured in different ways, and the circuit shown in FIG. 4 is only exemplary of one of the several possible circuits that can be used.

Figure 5:
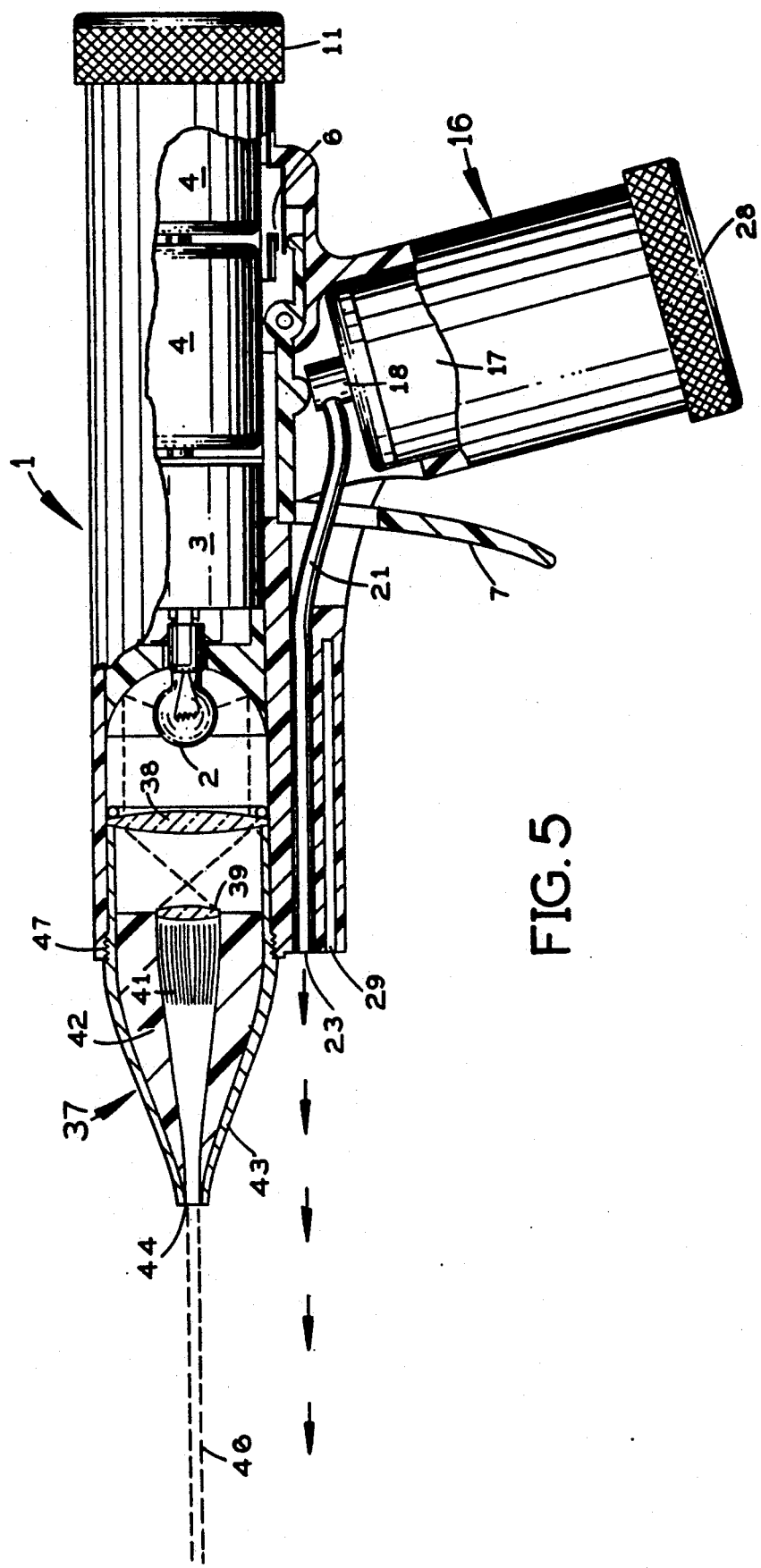
FIG. 5 is an elevational diagrammatic view of the invention showing an elongate nozzle for treating constricted areas.

FIG. 5 shows a version of the invention which is especially adapted to constricted body orifices. A UV-light concentrating optical assembly 37 includes a condensing lens 38 of UV-permeable material, which concentrates the UV light onto a small condensing lens 39 coupled to a bundle of optical fibers 41, advantageously suspended in a matrix 42 of suitable plastic material. The matrix 42 is confined in a conical funnel-shaped enclosure 43 terminating in a narrow outlet 44, which transmits a narrow beam 46 of UV-light that can be directed to a small infected area of a patient. 1- r, The optical assembly 37 is advantageously made interchangeable with condensing lens 14 seen in FIG. 1, by means of screw threads 47 that allow optical assembly 37 to be of variable focus or unscrewed from housing 1 and replaced by lens 14 with its containing ring 48.

In case only UV-light treatment is to be provided, the bottom screw cover 28 can be unscrewed a short distance so as to retract the aerosol can 17 a short distance from the cam 26 so that valve 18 is beyond reach of the trigger 17 with its cam 26 (FIG. 7).

FIG. 6 shows the invention having a tongue depressor 30 inserted in the slot 29.

I claim:

1. A bactericidal ultraviolet light radiating device for treatment of dermal tissues disposed in forward direction for the radiating device comprising an ultraviolet light source, optical light-directing means optically coupled to said ultraviolet light source for directing said ultraviolet light to said dermal tissues, electric power supply means connected to said ultraviolet light source for supplying electric power for said ultraviolet light source, a trigger in said electric power supply means for activating said power supply means, and medication dispensing means coupled to said trigger for dispensing mediation to said dermal tissues upon operation of said trigger.

2. A bactericidal ultraviolet radiation device according to claim 1, including a curved reflector disposed behind said ultraviolet light source in direction away from said dermal tissue in said optical light directing means.

3. A bactericidal ultraviolet radiating device according to claim 2 in which said reflector is adjustable to enlarge or restrict the area of radiation.

4. A bactericidal ultraviolet radiating device according to claim 1 including an optical condensing lens disposed in forward direction of said ultraviolet light source in said light-directing means for condensing said ultraviolet light.

5. A bactericidal ultraviolet radiating device according to claim 4 in which said condensing lens is a zoom lens.

6. A bactericidal ultraviolet radiating device according to claim 1, including a curved reflector disposed behind said ultraviolet light source and an optical condensing lens disposed in forward direction of said ultraviolet light source in said optical light-directing means.

7. A bactericidal ultraviolet radiating device according to claim 1, wherein said medication is selected from the group of medications consisting of antiseptics, anesthetics, antibiotics, salve solutions and soothing agents or combination thereof.

8. A bactericidal ultraviolet radiating device according to claim 1, including an aerosol dispenser in said mediation dispensing means, a pressure-sensitive valve on said aerosol dispenser, said trigger coupled to said valve for activating said valve, and a forward facing spray nozzle connected to said valve for forwardly directing a spray of said medication upon activation of said trigger.

9. A bactericidal ultraviolet radiating device according to claim 8, including a container for containing said aerosol dispenser, and a retractable screw cover at the bottom of said container for retracting said dispenser from engagement with said trigger.

10. A bactericidal ultraviolet radiating device according to claim 1, including a power converter in said electric power supply means, and at least one electric battery connected to said power converter.

11. A bactericidal ultraviolet radiating device according to claim 10, wherein said electric power supply means include an electric storage battery.

12. A bactericidal ultraviolet radiating device according to claim 1, including an electric switch connected to said electric power supply means, and activating linkage coupling said trigger means to said electric switch.

13. A bactericidal ultraviolet radiating device according to claim 1, including light concentrating means in said optical light directing means.

14. A bactericidal ultraviolet radiating device according to claim 13, including optical fiber conducting means in said light concentrating means for concentrating light to a thin ray of ultraviolet light.

15. A bactericidal ultraviolet radiating device according to claim 1, including a forward-facing slot in said radiating device for holding a tongue depressor in said slot.

* * * * *